United States Patent
Rolfs et al.

(10) Patent No.: US 9,125,999 B2
(45) Date of Patent: Sep. 8, 2015

(54) DRY POWDER INHALER DOSE COUNTERS

(75) Inventors: Bryan E. Rolfs, Chicago, IL (US);
Benjamin L. Rush, Wilmette, IL (US);
Jonathan D. Toback, Chicago, IL (US);
Peter D. Hodson, Breaston (GB);
Stephen W. Stein, Lino Lakes, MN (US); Michael K. Domroese, Woodbury, MN (US)

(73) Assignee: Adamis Pharmaceuticals Corporation, San Diego, CA (US)

( * ) Notice: Subject to any disclaimer, the term of this patent is extended or adjusted under 35 U.S.C. 154(b) by 937 days.

(21) Appl. No.: 13/320,761

(22) PCT Filed: May 17, 2010

(86) PCT No.: PCT/US2010/035129
§ 371 (c)(1),
(2), (4) Date: Mar. 6, 2012

(87) PCT Pub. No.: WO2010/135253
PCT Pub. Date: Nov. 25, 2010

(65) Prior Publication Data
US 2012/0152245 A1    Jun. 21, 2012

Related U.S. Application Data

(60) Provisional application No. 61/179,231, filed on May 18, 2009.

(51) Int. Cl.
*A61M 15/00* (2006.01)
*A61M 16/00* (2006.01)
*G06M 1/04* (2006.01)

(52) U.S. Cl.
CPC ....... *A61M 15/0045* (2013.01); *A61M 15/0008* (2014.02); *A61M 15/0026* (2014.02);
(Continued)

(58) Field of Classification Search
CPC ............... A61M 15/0026; A61M 15/0028; A61M 15/0045; A61M 15/0051; A61M 15/0065; A61M 15/0068; A61M 15/007; A61M 15/0071; A61M 15/0073; A61M 15/0075; A61M 15/0076; A61M 15/0078; G06M 1/04; G06M 1/045
USPC ................ 128/203.12, 203.15, 203.21
See application file for complete search history.

(56) References Cited

U.S. PATENT DOCUMENTS 4,317,385 A * 3/1982 Harvey et al. .............. 74/436
5,408,994 A   4/1995 Wass et al.
(Continued)

FOREIGN PATENT DOCUMENTS

EP   0 705 614   4/1996
EP   1 386 630   2/2004
(Continued)

OTHER PUBLICATIONS

D. Ganderton et al.; "Drug Delivery to the Respiratory Tract"; Chapter 9—The formulation and evaluation of pressurised metered-dose inhalers: published by Ellis Horwood, Chichester; 1987; pp. 87-118.

*Primary Examiner* — Valerie L Skorupa
*Assistant Examiner* — Douglas Sul
(74) *Attorney, Agent, or Firm* — K&L Gates LLP; Louis C. Cullman; Robert W. Winn

(57) ABSTRACT

Dry powder inhaler dose counters capable of making a display move swiftly between digits, in contrast to the progressive movement that occurs in simple gearing mechanisms.

16 Claims, 17 Drawing Sheets

(52) U.S. Cl.
CPC ....... *A61M15/0043* (2014.02); *A61M 15/0051* (2014.02); *A61M 15/0055* (2014.02); *A61M 15/0065* (2013.01); *A61M 15/0075* (2014.02); *G06M 1/04* (2013.01); *G06M 1/045* (2013.01); *A61M 15/0091* (2013.01); *A61M 2202/064* (2013.01)

(56) References Cited

U.S. PATENT DOCUMENTS

| | | | |
|---|---|---|---|
| 5,564,414 | A | 10/1996 | Walker et al. |
| 5,582,162 | A | 12/1996 | Petersson |
| 5,590,645 | A | 1/1997 | Davies et al. |
| 5,619,984 | A | 4/1997 | Hodson et al. |
| 7,107,988 | B2 | 9/2006 | Pinon et al. |
| 7,322,352 | B2 | 1/2008 | Minshull et al. |
| 8,113,199 | B2 * | 2/2012 | Augustyn et al. ........ 128/205.23 |
| 8,181,645 | B2 * | 5/2012 | Houzego et al. ......... 128/203.15 |
| 8,245,906 | B2 * | 8/2012 | Crosby et al. ............... 235/91 R |
| 8,746,242 | B2 * | 6/2014 | Connell et al. ........... 128/203.21 |
| 2004/0255935 | A1 * | 12/2004 | Bruna ...................... 128/200.23 |
| 2009/0101150 | A1 * | 4/2009 | Stradella et al. ......... 128/205.23 |

FOREIGN PATENT DOCUMENTS

| | | |
|---|---|---|
| WO | WO 94/12230 | 6/1994 |
| WO | WO 97/24586 | 7/1997 |
| WO | WO 98/52634 | 11/1998 |
| WO | WO 99/57019 | 11/1999 |
| WO | WO 2004/026380 | 4/2004 |
| WO | WO 2005/002654 | 1/2005 |
| WO | WO 2005/079727 | 9/2005 |
| WO | WO 2007/103715 | 9/2007 |
| WO | WO 2007/112267 | 10/2007 |
| WO | WO 2007/122358 | 11/2007 |

* cited by examiner

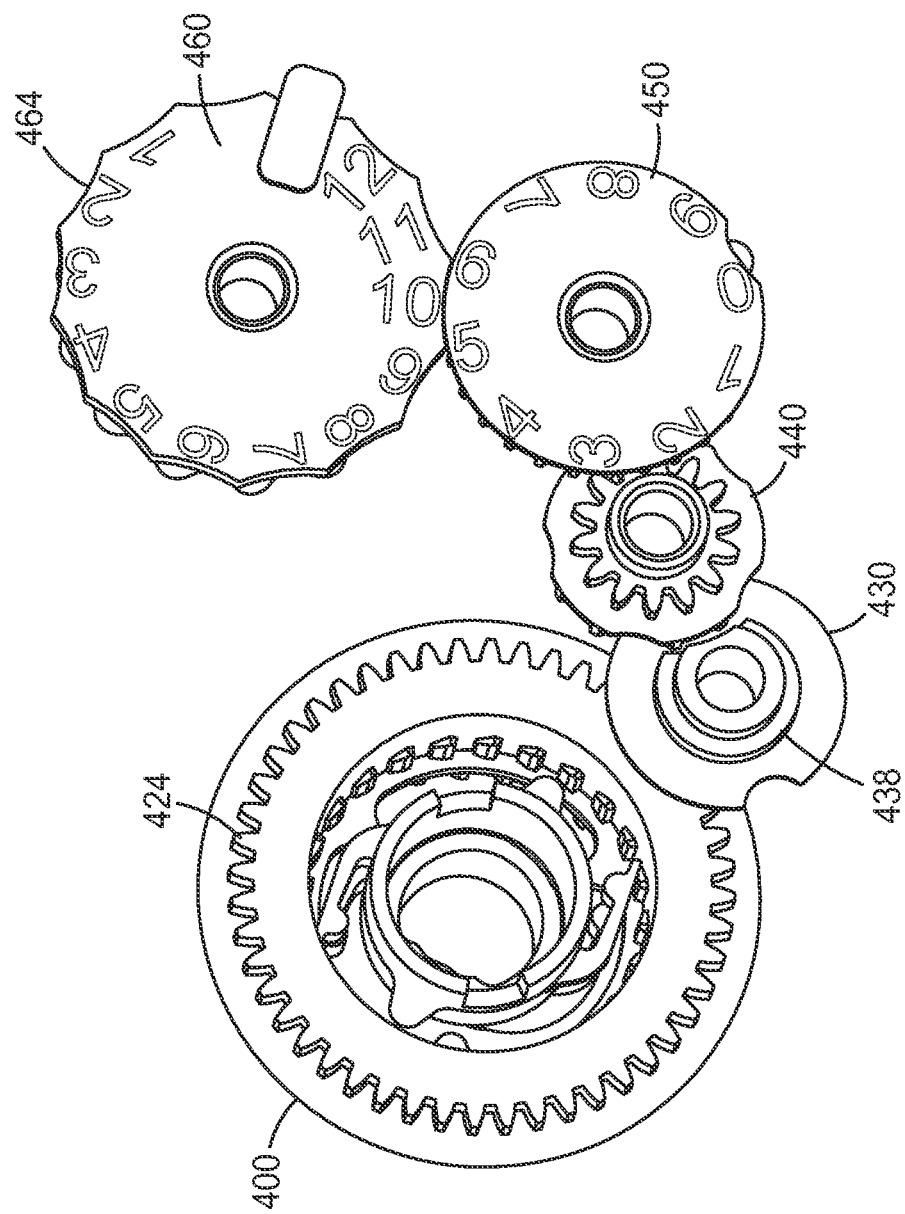

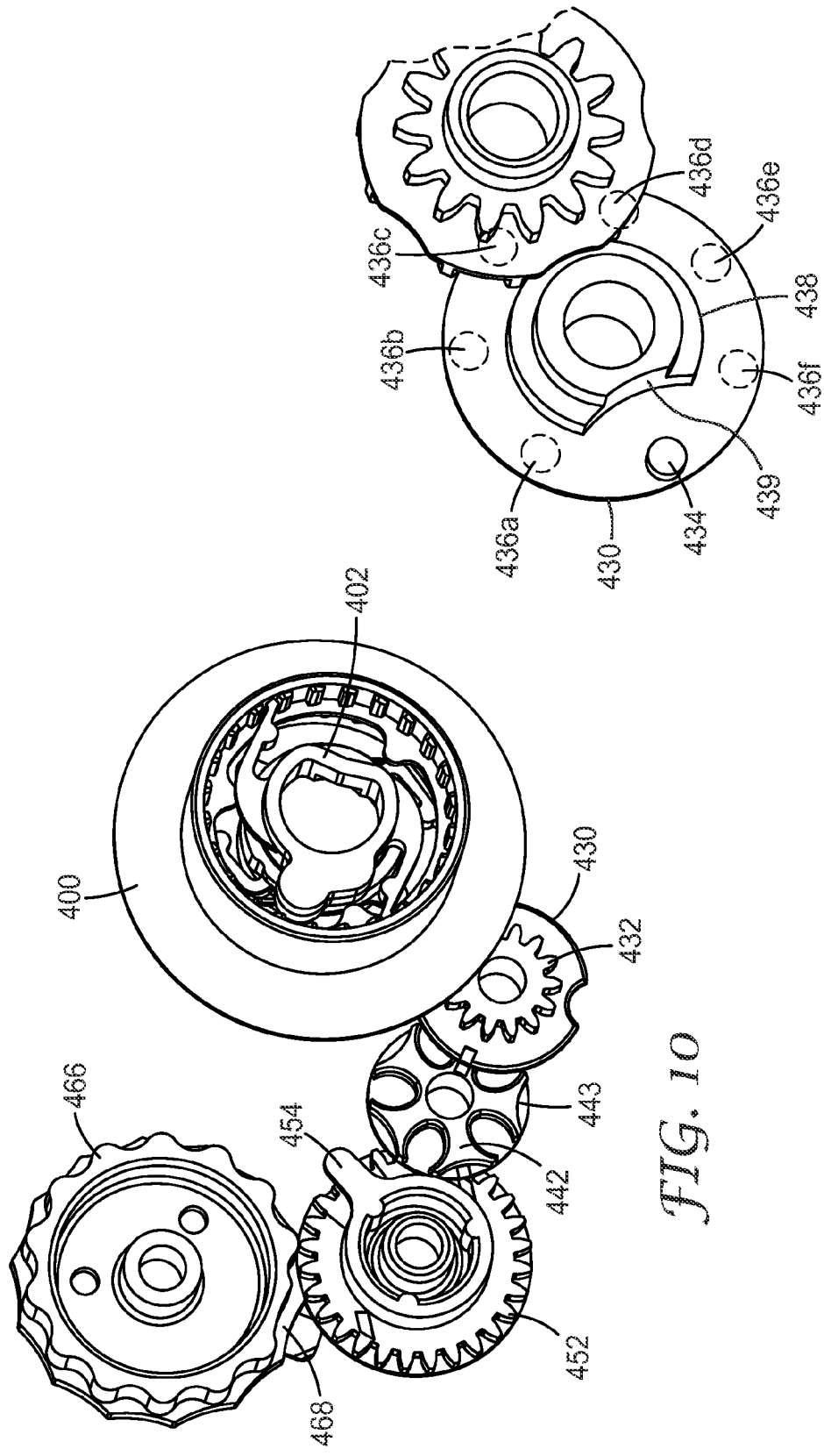

DRY POWDER INHALER DOSE COUNTERS

CROSS-REFERENCE TO RELATED APPLICATIONS

This application is the U.S. national stage of PCT application No. PCT/US2010/035129, filed May 17, 2010, which claims priority to U.S. Provisional Application No. 61,179,231, filed May 18, 2009. The contents of each application are hereby incorporated by reference in their entireties.

FIELD

This application relates to dry powder inhalers (DPIs) and in particular, to dose counters for dry powder inhalers.

BACKGROUND

Asthma and other respiratory diseases have long been treated by the inhalation of appropriate medicaments. For many years the two most widely used and convenient choices of treatment have been the inhalation of medicament from a drug solution or suspension in a pressurized metered dose inhaler (pMDI), or inhalation of powdered drug, generally admixed with an excipient, from a dry powder inhaler (DPI). Following strong concern about the link between depletion of the earth's ozone layer and chlorofluorocarbon (CFC) emissions, the use of these materials in pressurized inhalers is being phased out and interest in DPI systems has been stimulated.

Current regulatory guidance in some parts of the world recommends that a medicinal inhaler include a dose-counting device so that a patient may be aware when a device is nearing the end of its recommended number of actuations. It is desired that a dose counter be as nearly 100 percent reliable as possible and, in particular, that a device avoid undercounting. That is, the device should not deliver a dose without advancement of the counter, since this could lead a patient to believe there is more medication left in the device than actually remains.

Dose counters for dry powder inhalers are well known in the state of the art, including those described in, for example, U.S. Pat. No. 5,582,162 (Petersson), U.S. Pat. No. 5,590,645 (Davies et al.), U.S. Pat. No. 7,107,988 (Pinon et al.), U.S. Pat. No. 7,322,352 (Minshull et al.), and WO 2005/079727 (Augustyn et al.). In practice most DPIs use either bulk powder reservoirs or individual pre-measured doses sealed within individual containers in the form of capsules or blisters, such as blister packs and blister strips. In a typical device with capsules or blisters it is generally sufficient to simply count the capsules or blisters one by one as the device is actuated and they are used. In a typical reservoir device there is generally a metering step, such as rotation of a dose cup from a position inside the reservoir to a position within an airflow chamber, and dose counting can be done by simply counting the number of rotations of the dose cup.

SUMMARY

According to one aspect of the present description there is provided a dry powder inhalation device comprising a housing defining a chamber, a patient port in communication with said chamber, an elongate carrier carrying medicament, an advancement mechanism for advancing a length of the elongate carrier into the chamber, a displacement sensor that advances in association with continuous advancement of the elongate carrier, and a transfer component that converts the advancement of the displacement sensor into intermittent motion of a units dose display.

The displacement sensor of a dry powder inhaler in accordance with the first aspect described herein may advantageously have a range of positions where it movably engages the transfer component. The inhaler may further comprise a discrete alignment mechanism capable of moving the displacement sensor backwards to one of a plurality of spatially defined positions that are not within said range of movably engaged positions. Dependent claims define further embodiments.

BRIEF DESCRIPTION OF DRAWINGS

In the accompanying drawings:

FIG. 10 represents an isometric near-to-rear view of a detailed portion of the exemplary device.

FIG. 11 represents an isometric near-to-front view of a detailed portion of the exemplary device.

DETAILED DESCRIPTION

A problem that had not previously been appreciated in the art is that, where a dry powder inhalation device dispenses medicament on an elongate carrier (e.g., an elongate strip) by length, counting of doses corresponding to dispensed lengths is not straightforward. Briefly, the count display can lodge between digits, leading to confusion of the user even if a display window large enough to show the digits on either side is employed.

Inhalation devices according to the description are able to make the display move swiftly between digits, in contrast to the progressive movement that would occur in simple gearing mechanisms. Where the operation of an inhalation device involves a repeated advancing movement e.g., movement of a spool taking up an elongate carrier bearing medicament for dosing, arranging for swift movement between digits of a dose counter engaged with the spool provides a display showing an individual units count digit, rather than units count digits slightly offset from a viewing window.

Certain embodiments of the description provide mechanisms to prevent the display getting out of step with the dosing due to accumulation of small variations in the advancement per dose, or due to the patient only partially advancing the dispensing mechanism. Such small variations can arise due to relative positions of ratchets and pawls at the end of a motion during which a pawl slips over a ratchet. Surprisingly, these embodiments employ larger variations in the relative positions of a pawl and a ratchet at the end of motion, and yet provide a precise count point in the dispensing operation at which digital advancement occurs. This allows either one digit or the next to be displayed even if a partial dispensing operation was performed close to this count point, whilst retaining a memory of what partial dose was dispensed in order to keep the tally accurate.

Thus, the dry powder inhalation devices of the description provide digital counting mechanisms that are accurate and do not lodge between digits during operation.

Figure 1:
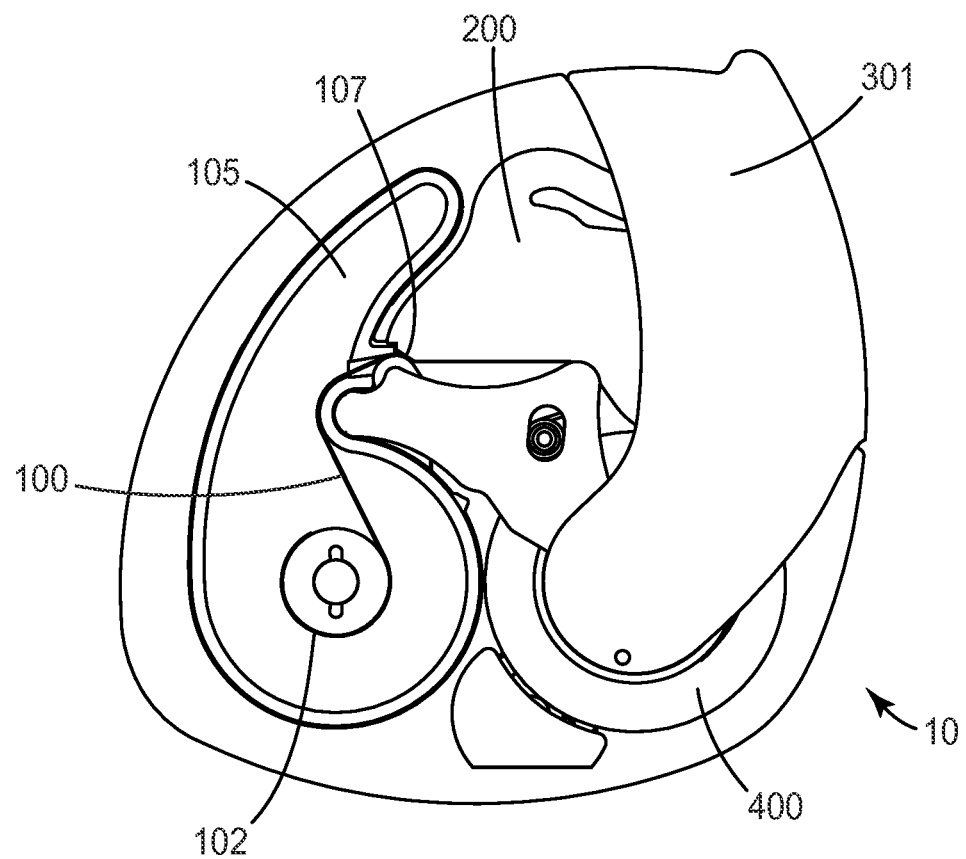
FIG. 1 represents a partial rear view of an exemplary device wherein the rear housing has been omitted for illustrative purposes.
Figure 2:
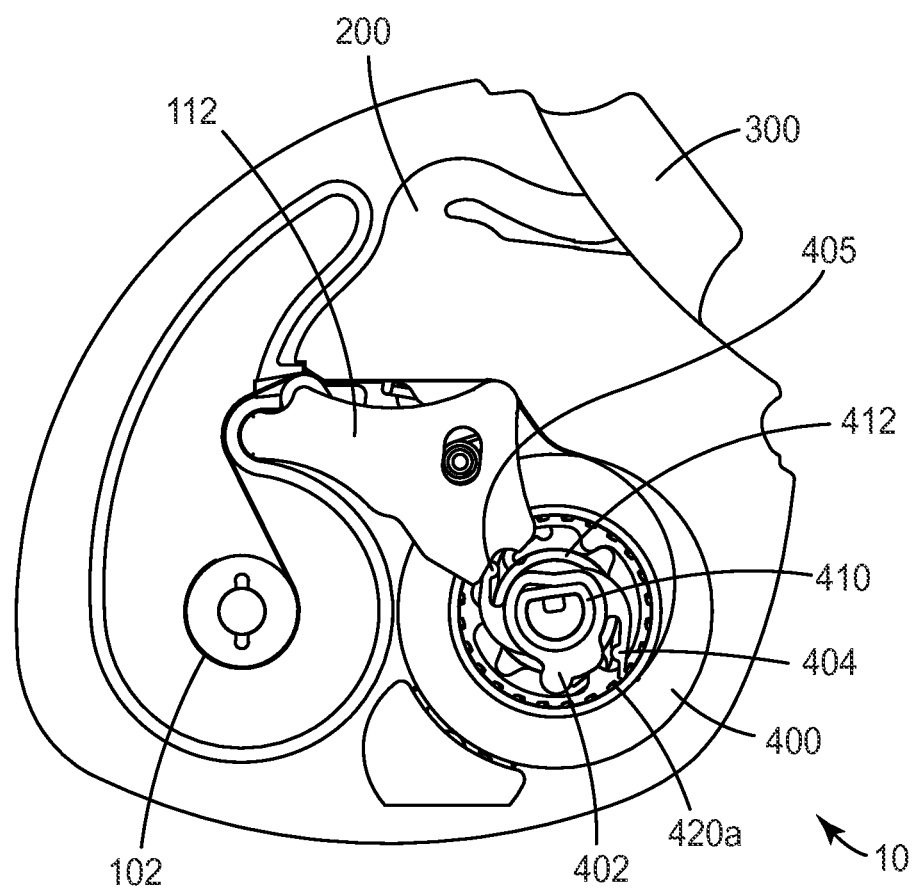
FIG. 2 represents a partial rear view of the exemplary device wherein the rear housing and mouthpiece cover have been omitted for illustrative purposes.
Figure 3:
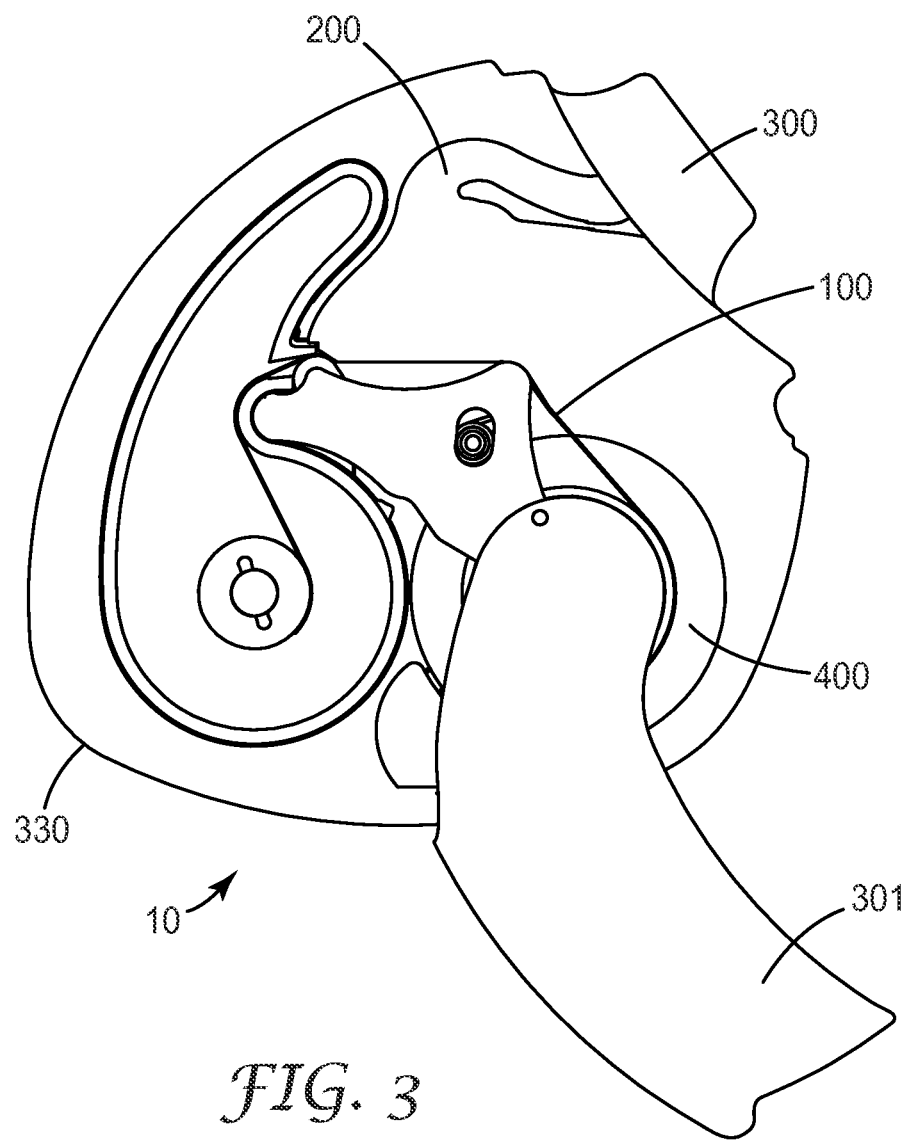
FIG. 3 represents a partial rear view of an exemplary device wherein the rear housing has been omitted for illustrative purposes and the device is shown with its mouthpiece cover in the fully opened position.

FIG. 1 represents a partial rear view of an exemplary dry powder inhaler (10) in its closed position wherein the rear housing has been omitted for illustrative purposes. FIG. 2 represents a corresponding view of the inhaler (10) wherein the mouthpiece cover (301) has been omitted. The inhaler (10) includes a flow chamber (200) and a patient port, in particular in the form of a mouthpiece (300), in communication with said chamber. The patient port is not visible in FIG. 1, because in the closed position of the illustrated inhaler the mouthpiece is covered by the cover (301), but it is shown in FIG. 3 in which the cover has been fully opened. The inhaler (10) also includes an elongate carrier (100) preloaded with finely divided powder comprising a biologically active substance (not visible). Preferably, the elongate carrier (e.g., an elongate strip) is in the form of a tape.

The elongate carrier can be provided in a variety of forms, such as a tape, web, belt or cord. Desirably the carrier is provided in the form of a tape or a web. The elongate carrier may have any ratio of length to width but the ratio is generally greater than 5 to 1, usually greater than 10 to 1, more particularly from about 100:1 to about 1000:1. The elongate carrier may typically have a width of 5 mm to 20 mm, e.g., 10 mm. Its thickness may typically be from 75 microns to 500 microns, particularly 100 microns to 250 microns, more particularly from about 120 microns to 175 microns. Optionally, the elongate carrier may be provided with a lid component, for example to cover and/or seal off individual doses preloaded on the carrier.

The powder comprising a biologically active substance, typically a medicament, is releasably retained on a surface of the elongate carrier. The powder may be retained on the elongate carrier by attraction forces, such as electrostatic attraction, van der Waals forces, physical attraction; mechanical binding; and/or wedging. Alternatively as indicated supra powder may be retained on the elongate carrier by covering the powder using a lid component; however it is desirable not to have the pre-loaded powder on the elongate carrier covered and sealed with a lid component. To facilitate favorable release characteristics, it is desirable not to retain the powder on the elongate carrier via adhesives or glues. The aforesaid expression "mechanical binding" generally refers to powder particles being held onto the elongate carrier by intrinsic mechanical means of the elongate carrier material, e.g., within the entanglement of fibers of a nonwoven web. The expression "wedging" generally refers to loading powder particles within/into particular structures of the elongate carrier (e.g., micro-dimples provided in a plastic elongate carrier, or porous spaces of a nonwoven elongate carrier). One or more surfaces of the elongate carrier and optionally the interior of the elongate carrier may be configured to assist in retaining the particles of powder.

An elongate carrier may be constructed from one or more of a wide range of natural and synthetic materials e.g., polyethylene, polypropylene, polyester e.g., polyethylene terephthalate, polytetrafluoroethylene or a co-polymer thereof, ethylene vinyl alcohol, or cellulose. The materials may be in the form of non-woven fibrous materials, loose weave materials or fabrics, materials having a surface pile, films, microporous materials, microgrooved materials, cords of twisted fibers, or any other suitable material or composites of more than one material. Desirably an elongate carrier is constructed of a material or a material composite where small surface depressions, dimples, grooves, recesses, interstices, apertures or embossed surface structures having a typical size of equal to or less than 500 microns in either depth or height and of greater than 0.1 microns in at least one other dimension are provided to help to retain the particles of powder. Various materials for elongate carriers as well as particular forms of carriers suitable for use herein are disclosed in U.S. Pat. No. 5,619,984 (Hodson et al.), the contents of said patent in its entirety being incorporated here by reference.

Finely divided powders used in the devices described herein generally have a mass median particle diameter of 10 microns or less. More suitably, said mass median diameter is 7 microns or less, even more suitably 5 microns or less, and most suitably said mass median diameter is in the range 1 to 3 microns, with at least 90% by mass of the particles having diameters below 5 microns.

The powders may be micronized, e.g., by (i) using a fluid energy mill driven by compressed air, such as shown in 'Drug Delivery to the Respiratory Tract' ed. D. Ganderton and T. Jones, publ. Ellis Horwood, Chichester (1987) pages 89-90, or (ii) by repeated stepwise millings or (iii) by use of a closed loop milling system.

As indicated supra, desirably finely divided powder is filled into a plurality of microdepressions in the surface of an elongate carrier, in particular a flexible elongate carrier, such as a web or a tape. Depressions may be suitably spaced at an interval of about 20 to 2000 microns, more suitably at an interval of about 300 to 2000 microns. Depressions may suitably number from about 25 to 1000 per $cm^2$ of the web. The volume of each depression and the spacing or number of the depressions will depend upon the particular desired application of the resulting filled web and/or elongate carrier, and in the case of biologically active substances (e.g., medicaments) the potency of the particular substance and the area of the web material intended to provide a single dose of the substance. As the web will typically have a fixed width, one may refer to a corresponding length of web material intended to provide a single dose of substance.

Typically it is desirable that the elongate carrier material (e.g., web material) has a substantially uniform depression volume per unit area when considered on a scale of the area of a single dose or other functional unit. For example, such a dose area might have 200 to 2000 discrete microdepressions, each of about 45 microns depth and about 150 microns diameter. Advantageously, the rows of microdepressions along the longitudinal axis of the elongate carrier do not lie exactly parallel with the axis, but instead lie skewed at a small angle (e.g., 0.5° to 2°) to it, in order to avoid "quantization effects" caused by lateral variability in the slitting positions. The skew angle can be chosen appropriate to the microdepression spacing distance and the desired slit width, such that an exact total micro-depression volume is present on each (e.g., 20 mm×10 mm) dose area, no matter where slitting occurs, laterally.

Preferably, the microdepressions are provided by cast embossing of a low density polyethylene (LDPE) layer using a photolithographically patterned and etched, or a diamond machined, patterning roller. Suitably, the aforesaid LDPE layer is provided on a paper backing or a paper/LDPE laminate backing (with the paper between the two LDPE layers).

Such filled elongate carriers are particularly conveniently used in the administration of biologically active substances, in particular medicaments by inhalation. Moreover, elongate carriers having microdepressions can be substantially accurately and uniformly filled with such finely divided powders e.g., through methods disclosed in WO 2007/112267 (Hodson and Wilby), the content of which is incorporated in its entirety by reference, thus allowing for accurate and uniform release of doses of biologically active substances.

For delivery by inhalation, suitable medicaments include any drug or combination of drugs that may be administered by inhalation, that is a solid or that may be incorporated in a solid carrier. Suitable drugs include those for the treatment of respiratory disorders, e.g., bronchodilators, anti-inflammatories (e.g., corticosteroids) anti-allergies, anti-asthmatics, anti-histamines, and anti-cholinergic agents. Other drugs such as anorectics, anti-depressants, anti-hypertensive agents, anti-neoplastic agents, anti-tussives, anti-anginals, anti-infectives (e.g., antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins and sex hormones, vaccines and other therapeutic proteins and peptides may be employed for delivery by inhalation.

It is preferred for delivery by inhalation that the medicament employed exhibits a potency which permits a single dose to be loaded onto the elongate carrier in an area of less than about 25 cm$^2$ and preferably less than about 5 cm$^2$. More preferred is an elongate carrier containing a drug in such a manner and of such a type that between 0.25 and 2.5 cm$^2$, most preferably between 1.5 and 2.25 cm$^2$, of the elongate carrier will contain a single dose when used in a device such as those described in U.S. Pat. No. 5,408,994 or 5,619,984. Stated differently, given that a filled elongate carrier may conveniently carry between about 25 and 500 μg of powder per cm$^2$, the potency of the medicament will preferably be such that a single dose may be carried on the above-stated 0.25 to 2.5 cm$^2$ of elongate carrier.

Exemplary drugs which may be employed for delivery by inhalation include but are not limited to: albuterol, levalbuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, daratropium, aclidinium, glyciopyrronium, beclomethasone, betamethasone, butixocort, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, arformoterol, procaterol, indacaterol, TA2005 (carmoterol), omalizumab, montelukast, zafirlukast, betamethasone sodium phosphate, dexamethasone, dexamethasone sodium phosphate, dexamethasone acetate, prednisone, methylprednisolone acetate, oglemilast, zileuton, insulin, atropine, prednisolone, benzphetamine, chlorphentermine, amitriptyline, imipramine, clonidine, actinomycin c, bromocriptine, fentanyl, buprenorphine, pentamidine, calcitonin, leuprolide, alpha-1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol xinafoate, aclidinium bromide, glycopyrronium bromide, beclomethasone dipropionate, triamcinolone acetonide, fluticasone propionate, fluticasone furoate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, naltrexone, oxycodone, sufentanil, remifentanil, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isometheptene mucate, dichloralphenazone, sumatriptan, rizatriptan, zolmitriptan, naratriptan, eletriptan, barbiturates (e.g., pentobarbital, pentobarbital sodium, secobarbital sodium), benzodiazapines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocaine, xylocaine, beta-adrenergic blockers, calcium channel blockers (e.g., nifedipine, diltiazem hydrochloride, and the like), diuretics (e.g., amiloride, furosemide), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, loratidine, cyroheptadine hydrochloride, terfenadine citrate, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, reslizumab, mepolizumab, anrukinzumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g., pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, human growth hormone, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

The medicament may comprise one or more drugs, having one or more particulate forms, and may include one or more physiologically acceptable or inert excipients.

As shown in the exemplary embodiment illustrated in FIGS. 1 to 3, the elongate carrier (100) may be stored initially on a supply spool (102) and advanced onto an uptake spool (400) during use of the inhaler. In particular, the rotational motion of the mouthpiece cover (301) during opening is coupled to the uptake spool (400) and causes advancement of the elongate carrier (100). During use of the inhaler, in general, a portion of the elongate carrier is advanced to within the flow chamber so that the powder associated with an advanced length of the elongate carrier can be and is, upon actuation, released from the elongate carrier for inhalation by the patient through the patient port. In a preferred embodiment, a length of a predetermined size of the elongate carrier comprises a single dose of medicament.

A typical total length of elongate carrier would usually be greater than that shown on the supply spool in FIGS. 1 to 3, but the length shown is for ease of illustration. The elongate carrier (100) with its preloaded finely divided powder providing a plurality of doses is housed within a compartment (105), with the compartment being configured so that the preloaded doses are sealed within the compartment and such that the elongate carrier may be advanced from the compartment to the flow chamber (200) through an exit (107). As shown in FIGS. 1 and 2, where the inhaler is in its closed position, the exit (107) is closed on the elongate carrier. In use, however, the exit may be opened by movement of the pivoting component (112), which pivots downwards when the mouthpiece cover is opened.

Figure 4:
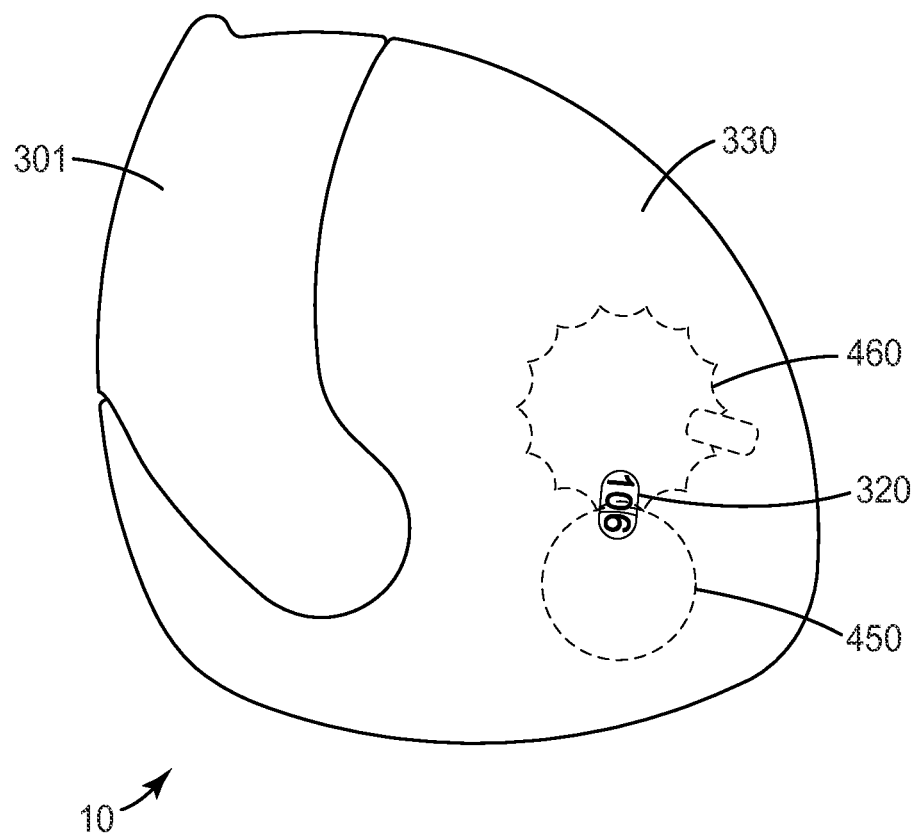
FIG. 4 represents a front view of the exemplary device, with the units wheel and tens wheel shown in outline.

As shown in FIG. 4, the inhaler includes a dose counter that indicates the number of doses remaining in the device which is visible through a window (320) in the outer housing (330). The dashed lines show the (hidden) positions of a units wheel (450) and a tens wheel (460) which cooperate to display a dose readout, in this case the number '106'. Further details of the operation of the dose counter will be described with reference to FIGS. 5a,b,c to 9a,b,c.

Figure 5A:
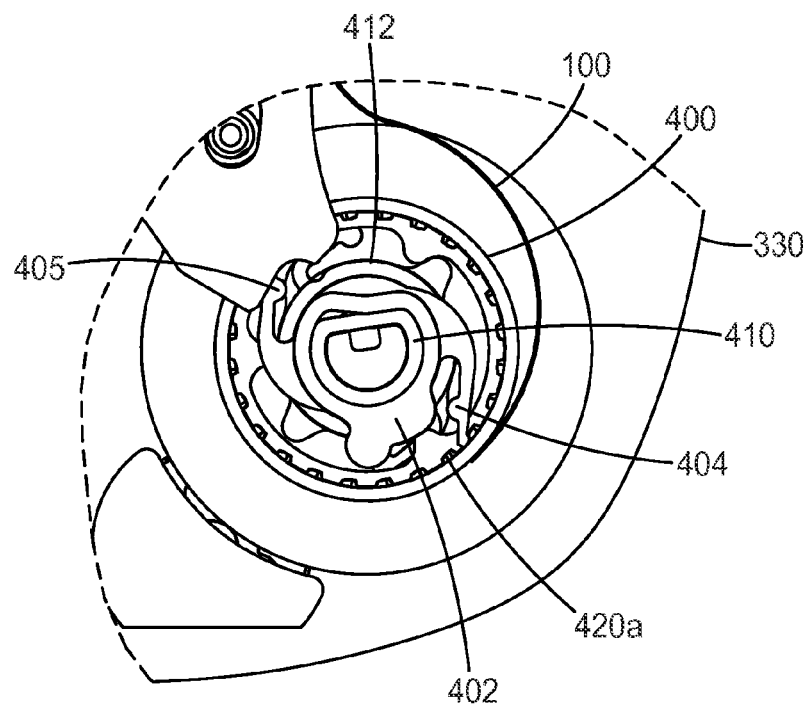
FIG. 5a represents a partial rear view of a detailed portion of the exemplary device in its closed position.
Figure 5B:
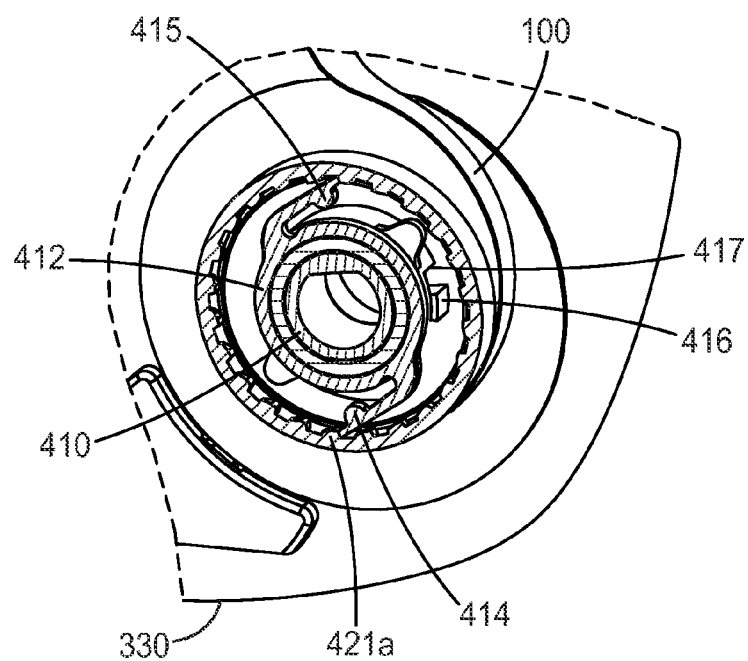
FIG. 5b represents a partial isometric near-to-rear cross sectional view of a detailed portion of the exemplary device in its closed position.

FIG. 5a represents a partial isometric near-to-rear view of a detailed portion of the inhaler in its closed position. The elongate carrier (100) is shown attached to an uptake spool (400). As described in more detail below, the uptake spool (400) may be driven forward or advanced (clockwise as drawn) by a forward pawl wheel (402) and in particular by two forward pawl wheel arms (404, 405) that engage with a first set of teeth (one tooth of which is denoted 420a) on the inner hub of the uptake spool (400) that serve as ratchet teeth. The uptake spool (400) may also be engaged by a reverse pawl wheel (412) having two reverse pawl wheel arms (414, 415) that may be better seen in the view shown in FIG. 5b. The reverse pawl wheel arms (414, 415) engage with a second set of ratchet teeth (one tooth of which is shown as 421a) on the inner hub of the uptake spool (400). The second set of ratchet teeth is also clearly visible in FIG. 5c and the tip of one tooth (420b) on the first set of ratchet teeth is just visible in FIG. 5c. The tip of tooth (420b) may be seen more clearly in FIG. 5d, which is an enlarged view of a detailed portion of FIG. 5c. Referring back to FIG. 5b, a post (416) that serves to limit the rotation of the reverse pawl wheel (412) is shown engaged with the lower (as drawn) surface of a slot (417) in the reverse pawl wheel (412). The post (416) has a fixed position in relation to the outer housing (330) and can thus be used to fix the extreme rotational positions of the reverse pawl wheel (412), in particular the extreme anticlockwise position shown in FIG. 5b, and to allow for limited movement of the reverse pawl wheel (412).

Figure 5C:
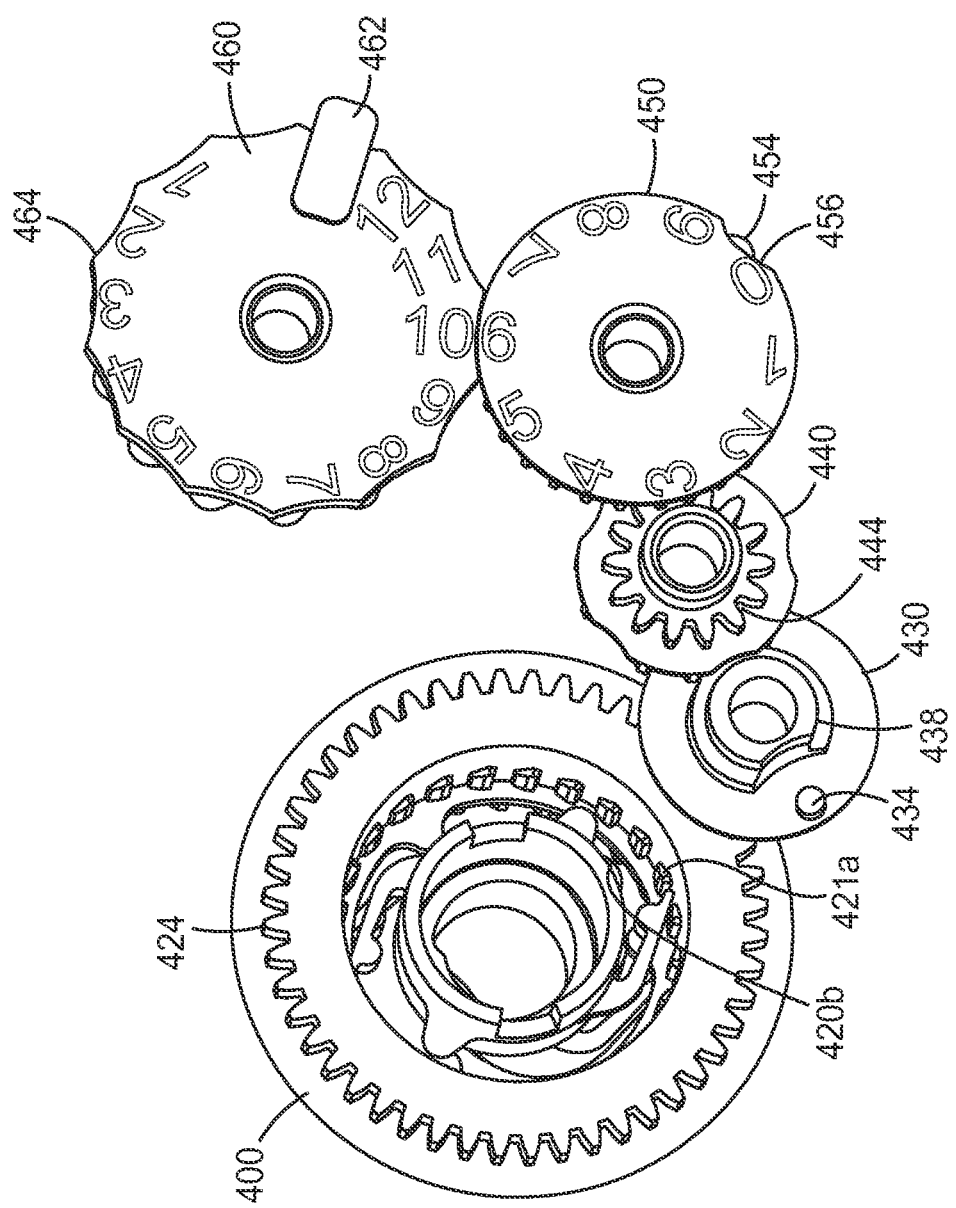
FIG. 5c represents an isometric near-to-front view of a detailed portion of the exemplary device in its closed position.
Figure 5D:
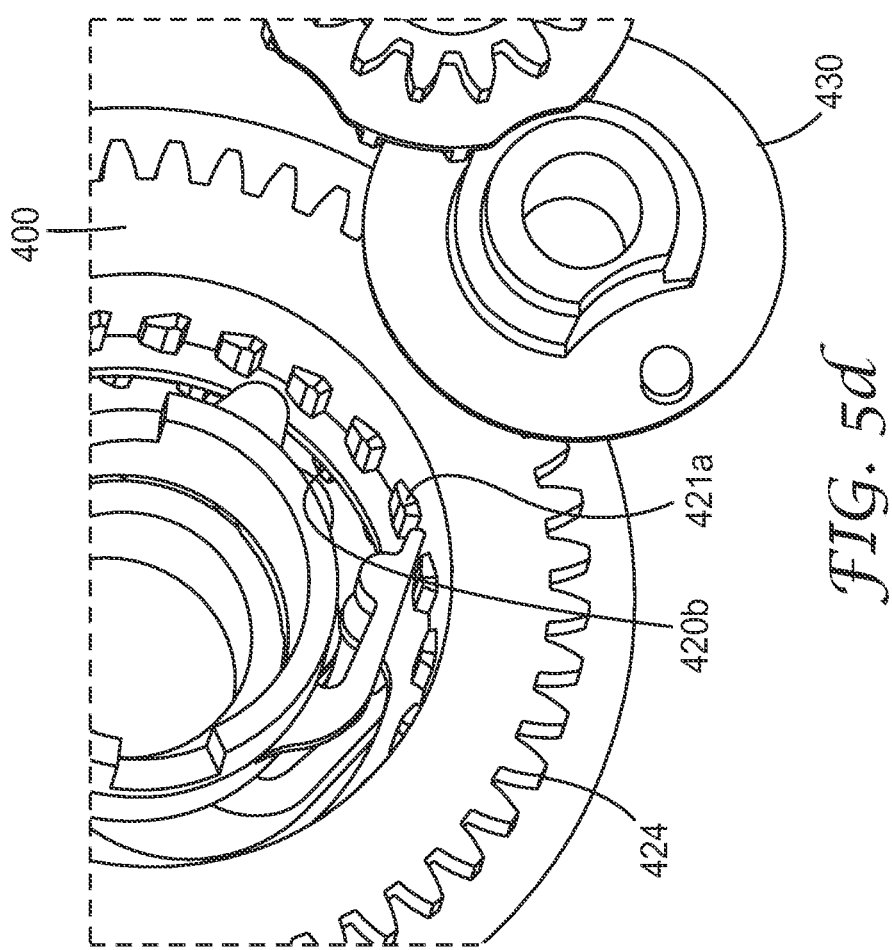
FIG. 5d represents an enlarged view of a detailed portion of FIG. 5c.

FIG. 5c represents an isometric near-to-front view of a detailed portion of the inhaler showing the relationship of the uptake spool (400) to the additional parts of the dose counting mechanism. The uptake spool (400) has spool gear teeth (424) that engage with sensor gear teeth (432) on the reverse side of a displacement sensor wheel (430), which may be seen in the rear view shown in FIG. 10. The displacement sensor wheel (430) can engage a Geneva wheel (440) through a pin (434) which can interact with lobes (442), shown in FIG. 10, on the reverse side of the Geneva wheel (440). The Geneva wheel (440) has concave cut-outs or scallops (443), shown in FIG. 10, along the outer edge of the lobes (442). These scallops (443) mate with a central hub (438) on the displacement sensor wheel (430), shown in FIG. 11 as well as FIGS. 5c-9c, and prevent the Geneva wheel (440) from rotating unless the displacement sensor wheel (430) is rotated so that the pin (434) is interacting with the Geneva wheel (440), in which alignment a cut-out region (439) allows the Geneva wheel (440) to rotate.

The Geneva wheel (440) can in turn drive a units wheel (450) via Geneva gear teeth (444) that interact with units wheel gear teeth (452), shown in FIG. 10, on the reverse side of the units wheel (450). The units wheel (450) has a tab (454) that is partially visible in FIG. 5c and fully visible in FIG. 10. The tab (454) will engage with tens wheel gear teeth (466), shown in FIG. 10, each time the units wheel (450) makes a complete revolution, thereby advancing the tens wheel (460) one position. The tens wheel (460) has a scalloped edge (464) that mates with the outer edge of the units wheel (450). This mating prevents rotation of the tens wheel (460) except for when it is being actively engaged by the tab (454) on the units wheel (450). This also provides an aesthetically pleasing display, since there is no gap in the background of the display that would otherwise be visible if both wheels (450, 460) had a circular circumference. A slight cut-out portion (456) is provided on the units wheel (450) to allow the tens wheel (460) to rotate freely when the tab (454) engages with it. The tens wheel is further provided with a paddle (462) and a missing gear tooth (468), shown in FIG. 10, whose functions will be described in greater detail below.

The general dose counting operation is as follows. Opening the mouthpiece cover (301) of the device advances the uptake spool (400) via movement of the forward pawl wheel (402). The uptake spool (400) and displacement sensor wheel (430) are sized and geared such that a full cycle of operation (i.e., opening the mouthpiece cover (301) fully and closing it again), which corresponds to a 105 degree rotation of the uptake spool (400), will cause a 360 degree rotation of the displacement sensor wheel (430). (This 360 degree rotation is that resulting from a full cycle. As will be explained below, a greater rotation in fact takes place, followed by a subsequent back-rotation to leave the net result as a 360 degree rotation.) The complete rotation of the displacement sensor wheel (430) causes the pin (434) to make a full revolution during which it engages a lobe (442) of the Geneva wheel (440) and causes the Geneva wheel (440) to step forward by an angular displacement equal to 360 degrees divided by the number of lobes of the Geneva wheel. As shown the Geneva wheel has 5 lobes, thus the angular displacement is 360/5 or 72 degrees. The Geneva wheel (440) and the units wheel (450) are sized and geared so that the 72 degree displacement of the Geneva wheel (440) corresponds to a 36 degree rotation of the units wheel (450) and thus advances (or decrements) the units wheel (450) by one number. As described above, the tab (454) on the units wheel (450) advances (or decrements) the tens wheel (460) by one number for each complete revolution of the units wheel (450). The tens wheel (460) is shown in FIG. 5c with markings and respective gear teeth (466), shown in FIG. 10, to allow a dose count for a 120-dose device, but it could clearly be re-sized and re-marked to provide counts for 30-dose, 60-dose, 200-dose, or any other desired number of doses. As shown the counter counts 'down', that is, it starts at the maximum number of doses in the device, displays the number of doses remaining, and counts down to zero, but it could equally be adjusted to count upwards from zero to show the number of doses that had been dispensed. As shown the tens wheel (460) has a blank space following the '1', so that as the counter changes from '10' to '9' it will only display the single digit '9'. Alternatively, the numeral '0' could be printed on the tens wheel so that the display would change from '10' to '09'. When the device has reached '0' it should be considered empty and discarded, but if another dose is advanced, then the units wheel (450) will rotate from '0' to '9', but the tens wheel (460) will rotate so that a paddle (462) covers the units wheel display. As shown in FIG. 10, a missing gear tooth (468) on the tens wheel (460) will subsequently prevent the tab (454) on the units wheel (450) from further engaging the tens wheel (460). Thus the units wheel (450) may continue to rotate indefinitely, but the paddle (462) will remain displayed in the window. The paddle (462) may be colored to match the outer housing of the device or may be colored to provide an indication that the device is empty (e.g., red). The paddle (462) may also be marked with indicia, such as '0', '00', 'X' or with instructions, such as 'empty', to provide further indication that the device is empty.

It should be understood that the same principles could be applied to inhalers with numerous variations to that described above. For example, the amount of tape advanced in a full cycle of operation need not be 105 degrees, but could instead be 90 degrees, 120 degrees, 150 degrees, or any other suitable amount of advancement. Although shown with 5 lobes, the Geneva wheel could have 4, 6, 10 or any suitable number of lobes, preferably with the gearing between the Geneva wheel (440) and units wheel (450) designed to advance the units wheel by 36 degrees per engaged lobe. Likewise, the displacement sensor could have multiple, equally-spaced pins and be geared such that a full cycle of operation would advance the displacement sensor by a rotation of 360 degrees divided by the number of pins (e.g., a 2-pin displacement sensor would rotate 180 degrees for each full cycle of operation). As shown, the forward pawl wheel arms (404,405) and the reverse pawl wheel arms (414, 415) engage with first and second sets of ratchet teeth, respectively, each of which has 24 equally spaced teeth that are aligned with the others set. Alternatively, a single set of 24 larger ratchet teeth could span the inner hub of the uptake spool and the forward and reverse pawl wheel arms would engage with that single set of teeth. Alternatively, different numbers of ratchet teeth, such as 18, 20, 30, 36, 40, 48, or any other suitable number could be employed. Also, the number of ratchet teeth on the two sets of ratchets may be equal or different. In one embodiment, the number of ratchet teeth on one set is an equal divisor of the number of ratchet teeth on the other set (e.g., a first set with 18 teeth and a second set with 36 teeth). In one embodiment, the number of ratchet teeth is an equal divisor of 360 (e.g., 12, 15, 18, 20, 24, 30, 36, etc.), such that equally spaced teeth are spaced apart by an integral number of degrees. However, the spacing of the second set of teeth is preferably sufficiently large to allow the uptake spool (400) to have a limited number of equally spaced closed positions of the kind shown in FIG.

5b, so that the resting locations of the pin (434) straddle the changeover interval of the Geneva wheel (440).

Further details of the interaction of the forward and reverse pawl wheels (402, 412) with the dose counting mechanism will be described with reference to FIGS. 5a,b,c to 9a,b,c. Several alignment features are evident in FIGS. 5a,b,c where the inhaler is in the mouthpiece cover closed position. The elongate carrier (100) has some slack in it. The forward pawl wheel arms (404,405) are not in driving engagement with any teeth on the uptake spool (400). In particular, it can be seen that forward pawl wheel arm (404) is not engaged with tooth (420a). The post (416) is protruding through and engaged with the lower part of slot (417). The reverse pawl wheel arms (414,415) are in engagement with ratchet teeth on the uptake spool (400). In particular, it can be seen that reverse pawl wheel arm (414) is engaged with tooth (421a). The pin (434) on the displacement sensor wheel (430) is 180 degrees rotated away (or directly opposed) from the Geneva wheel (440) and the units and tens wheels (450, 460) are cooperating to display the numeral '106'.

Figure 6A:
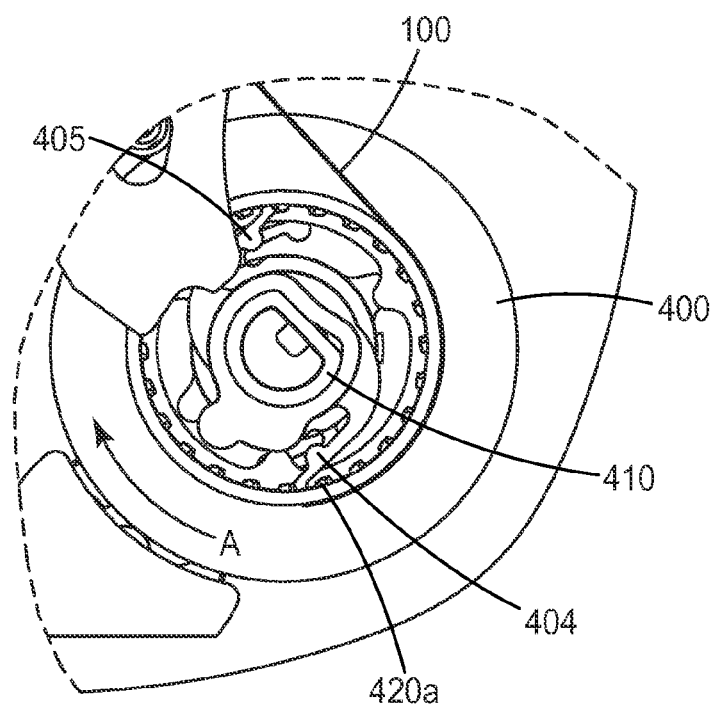
FIGS. 6a,b,c to 9a,b,c represent views corresponding to FIGS. 5,a,b,c at different positions between closed and fully open.
Figure 6B:
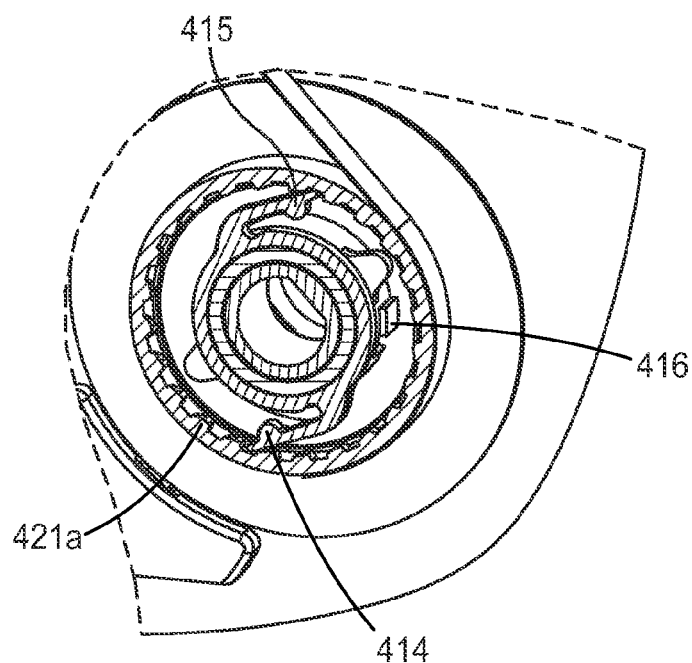
Figure 6C:
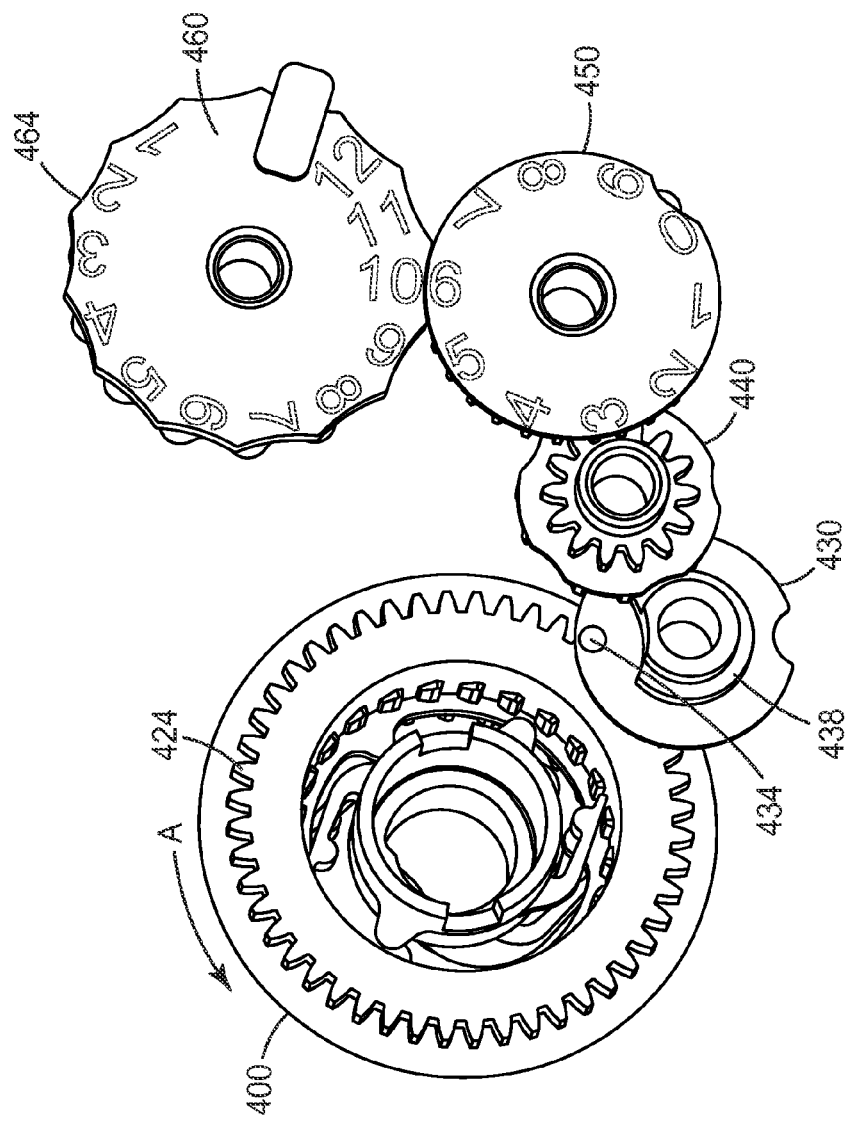
Figure 7A:
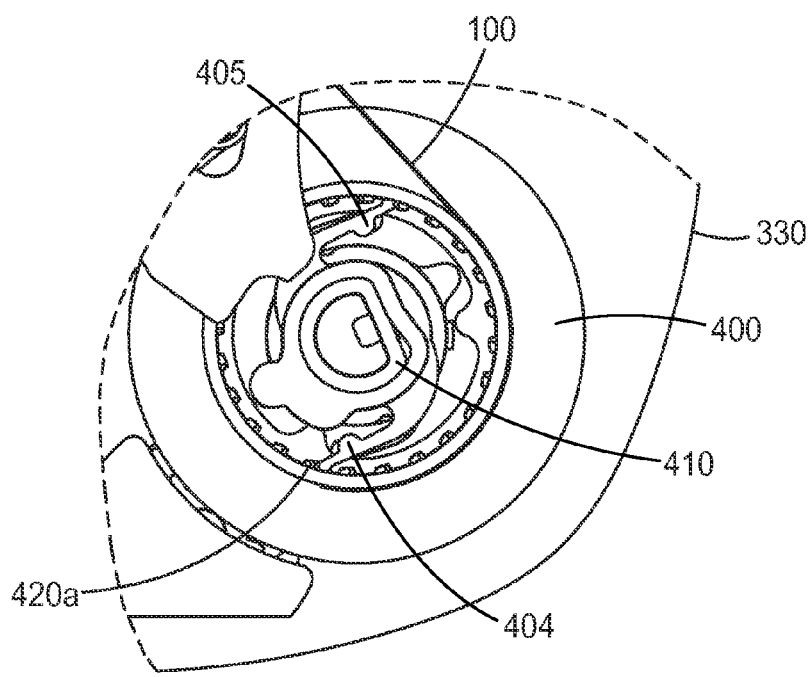
Figure 7B:
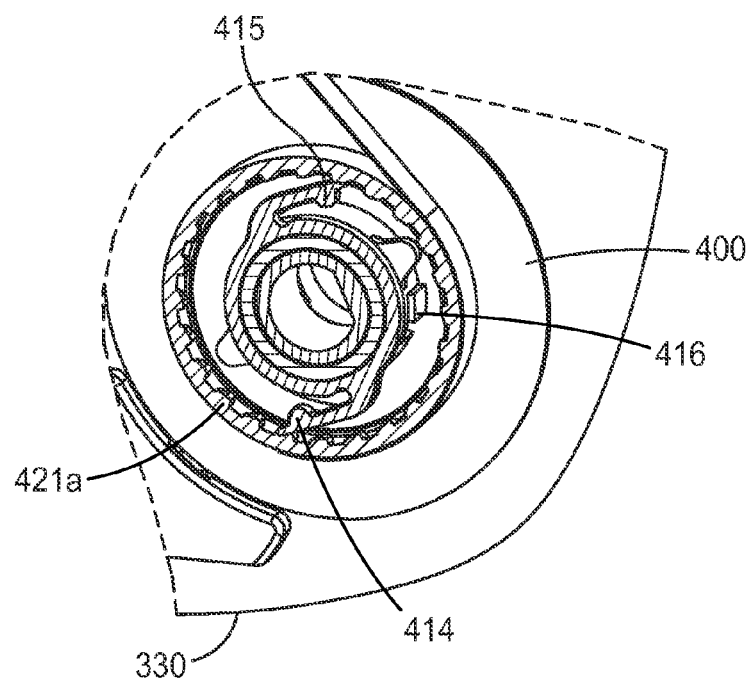

As the mouthpiece cover (301) is opened it rotates the cover pivot (410). After a flat side of the cover pivot has rocked over an inwardly-facing angled edge of the forward pawl wheel, the cover pivot rotates the forward pawl wheel (402) thus causing the forward pawl wheel arms (404,405) to come into engagement with the teeth on the uptake spool (400). In particular, as can be seen in FIG. 6a, which shows the inhaler in a position where the mouthpiece cover has been partially opened approximately 55 degrees, the forward pawl wheel arm (404) is now engaged with tooth (420a) and has rotated the uptake spool (400) forward in the direction of the arrow 'A', thus taking up the slack and advancing the elongate carrier (100). In addition, the reverse pawl wheel (412) is rotated by the uptake spool (400) approximately 15 degrees until the upper (as drawn) surface of the slot (417) comes into contact with the post (416), which prevents any further rotation of the reverse pawl wheel (412). Further forward rotation of the uptake spool (400) simply causes the reverse pawl wheel arms (414,415) to slip over the teeth (421) on the inner hub of the uptake spool (400). As can be seen in FIG. 6c, the uptake spool (400) rotation has caused a corresponding rotation of the displacement sensor (430), but has not yet brought the pin (434) into engagement with the Geneva wheel (440). The numeric display remains at '106'.

As the mouthpiece cover (301) is rotated further (in this case to approximately 75 degrees of opening) it can be seen (in FIG. 7c) that the pin (434) on the displacement sensor (430) has come into engagement with and partially rotated the Geneva wheel (440), although the pin (434) is now obscured by the Geneva wheel (440). Rotation of the Geneva wheel has caused the units wheel (450) to partially rotate. The uptake spool (400) and elongate carrier (100) are further advanced, but the engagement of the forward pawl wheel arms (404, 405) and the reverse pawl wheel arms (414,415) remains as described for FIGS. 6a,b,c. The numeric display shows the units digit partway between '6' and '5'.

Figure 8A:
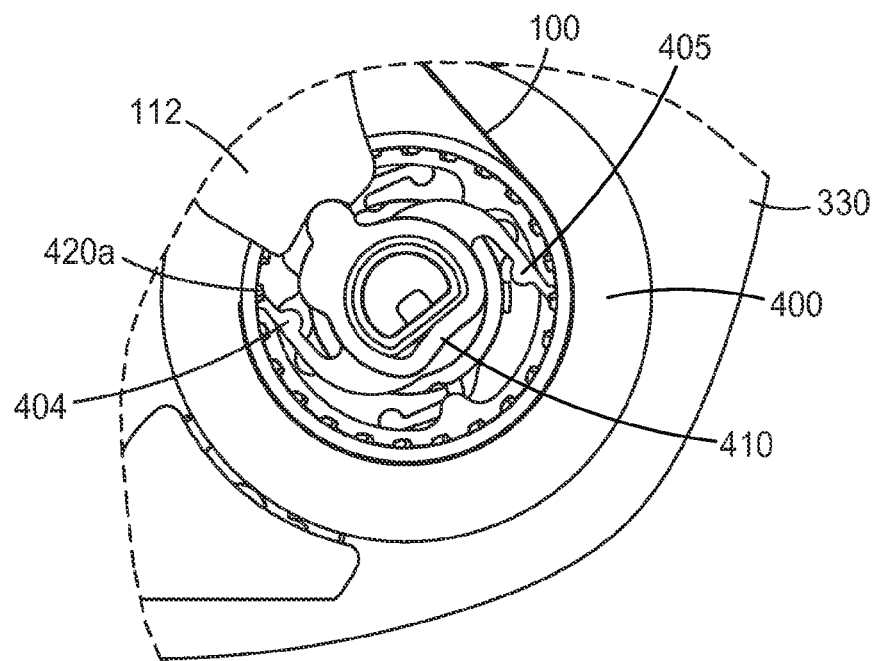
Figure 8B:
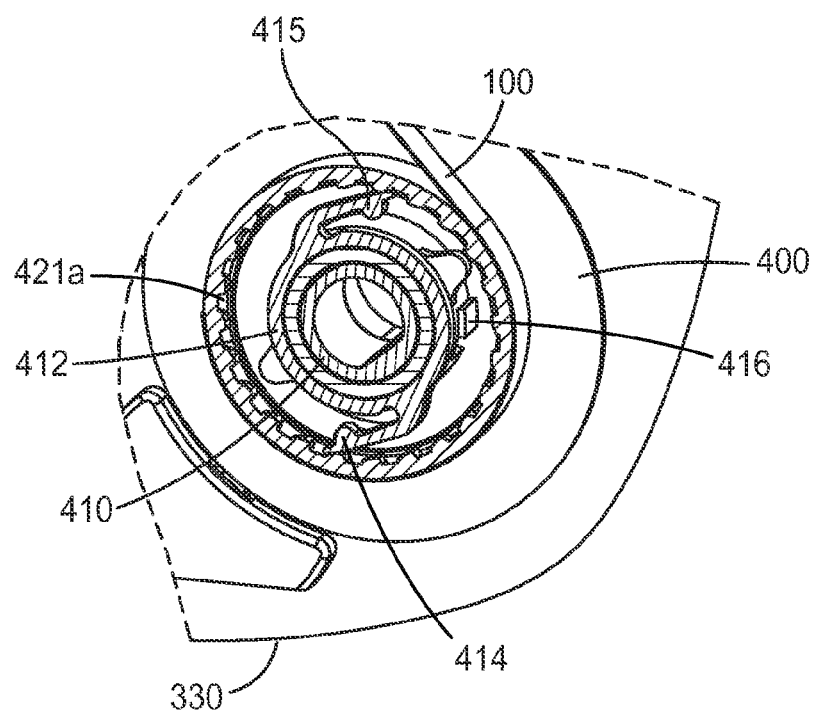
Figure 8C:
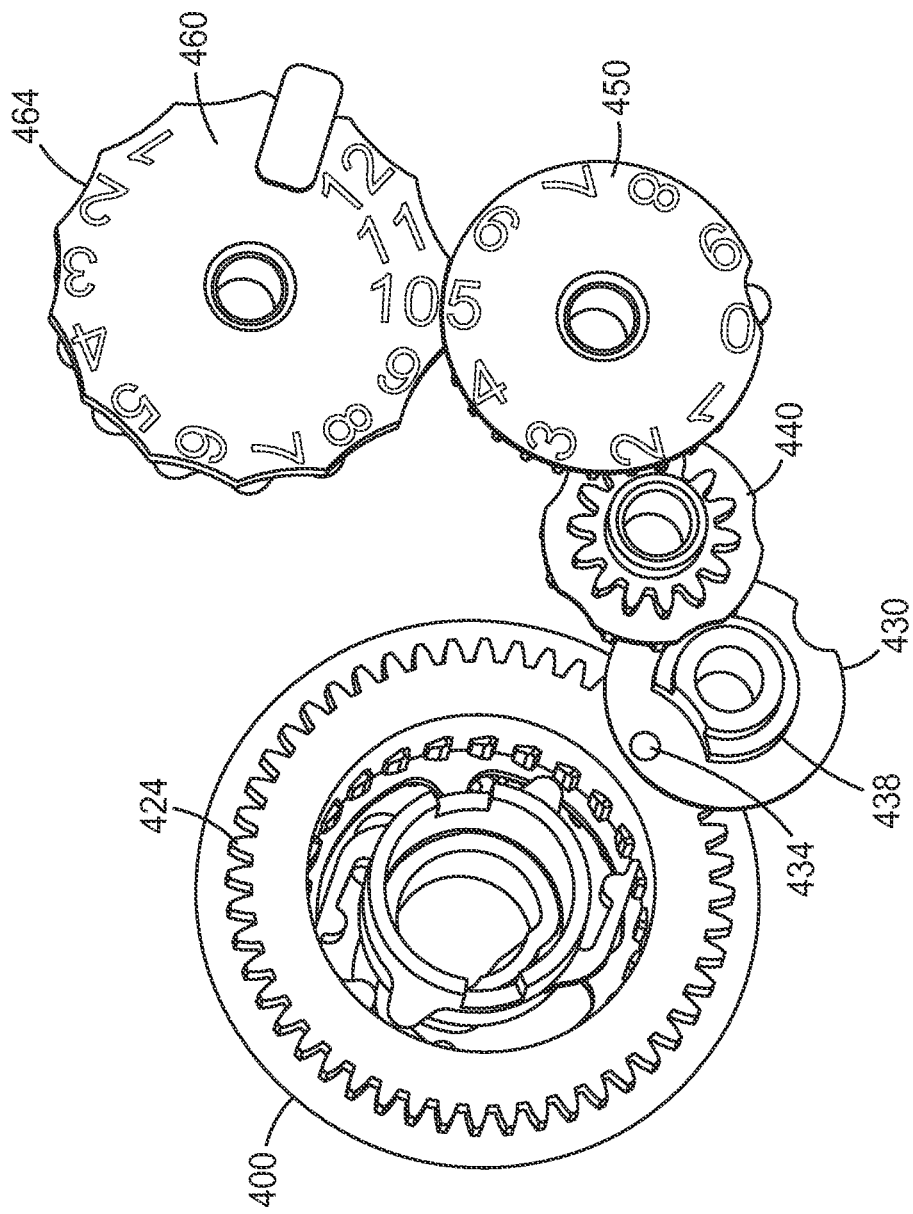
Figure 9A:
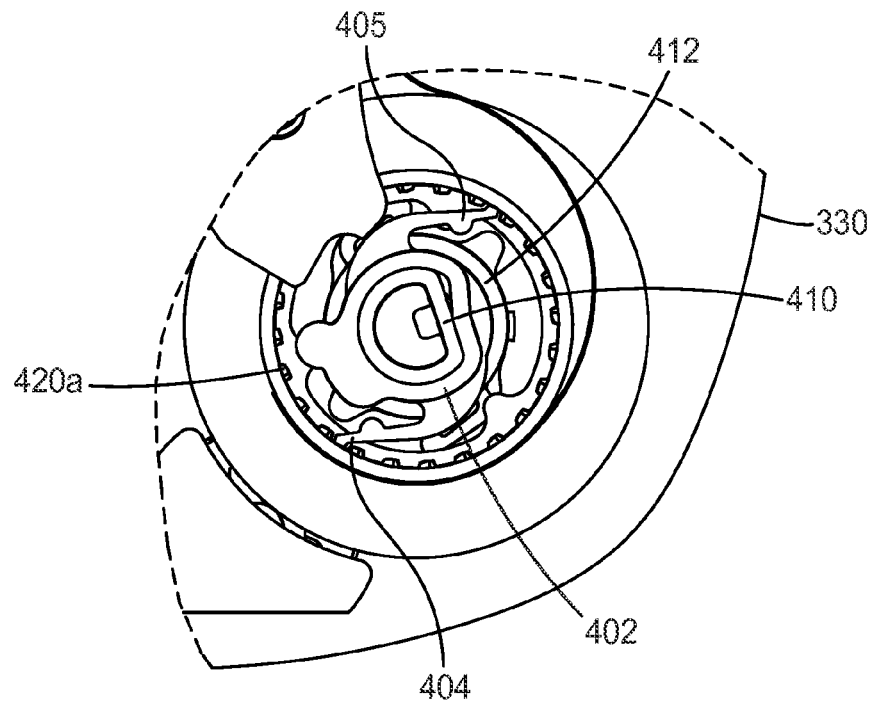
Figure 9B:
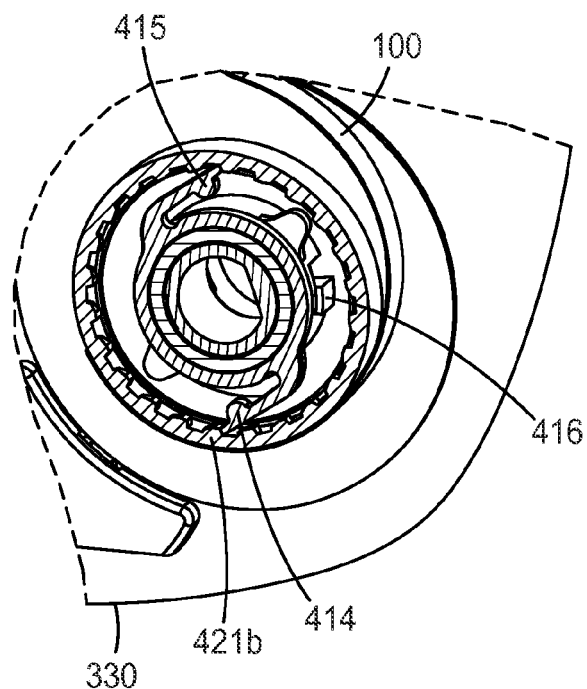
Figure 9C:
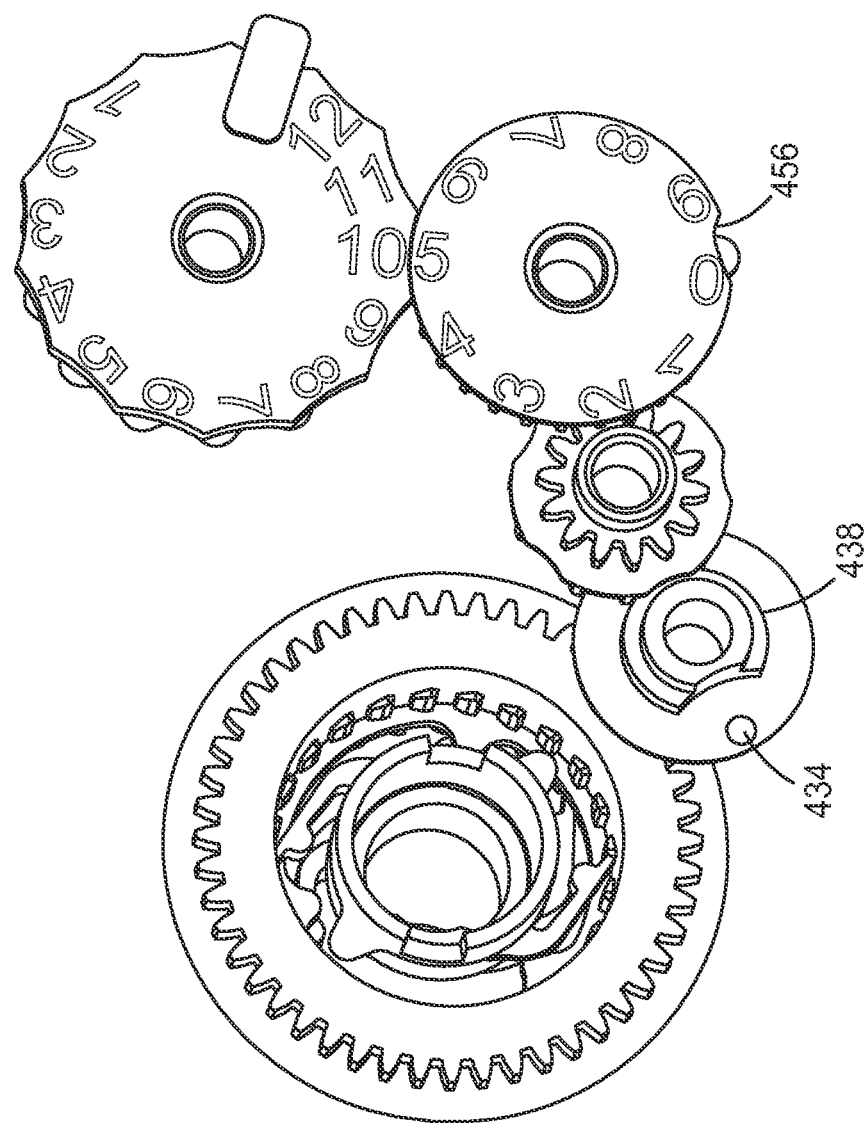

As the cover is more fully opened, the pin (434) on the displacement sensor (430) rotates past the Geneva wheel (440) after completing the advancement of the units wheel (450) to the numeral '5'. FIGS. 8a,b,c show the inhaler when the cover is in the fully open position. The elongate carrier (100) has been advanced one full dose. At this stage the pin (434) on the displacement sensor (430) has been rotated more than 360 degrees. Upon closing of the mouthpiece cover (301), however, the pin (434) on the displacement sensor (430) is rotated backwards so that it reaches the same orientation that it originally had in the cover closed position shown in FIG. 5c. This is shown in FIG. 9c at approximately the midpoint of the cover closing cycle. This fixed backwards rotation is effected by the reverse pawl wheel (412) as follows. As the cover is closed it initially rotates forward pawl wheel (402) backwards and the uptake spool (400) is allowed to rotate slightly backward. The backward rotation of the uptake spool (400) causes the spool ratchet teeth (421) to engage with the reverse pawl wheel arms (414,415). In particular, as shown in FIG. 9b, ratchet tooth (421b) engages reverse pawl wheel arm (414). Once engaged, further backward rotation of the uptake spool (400) by about 15 degrees causes backward rotation of the reverse pawl wheel (412) until the lower (as drawn) surface of the slot (417) in the reverse pawl wheel (412) comes into contact with the fixed post (416). This arrests motion of the reverse pawl wheel (412) and the uptake spool (400). At this point the reverse pawl wheel (412) has reached its original orientation as shown in FIG. 5b. Continued closing of the mouthpiece cover continues to rotate the forward pawl wheel (402) backwards towards its original orientation with the forward pawl wheel arms (404,405) slipping over the spool teeth (420), since the spool teeth are held fixed by the reverse pawl wheel (412). As shown in FIG. 9a, the forward pawl wheel arm (404) has rotated back a few teeth from the initial tooth (420a) that it was engaged with as it advanced the elongate carrier (100). The uptake spool (400) has been advanced forward 7 gear teeth corresponding to a complete dose. When the cover is fully closed the forward pawl wheel (402) will have returned to its original orientation as shown in FIG. 5a.

It is important to note that the position of the reverse pawl wheel is fixed when the mouthpiece cover is closed by virtue of one of the ratchet teeth on the uptake spool (400) pressing against the reverse pawl wheel arms (414, 415), in one direction and the lower surface of the slot in the reverse pawl wheel (412) pressing against the fixed post (416) in the other direction. As exemplified above, the uptake spool (400) has 24 ratchet teeth (421a,b, . . . ) that are spaced at 15 degree intervals from their neighbors and that interact with the reverse pawl wheel arms (414, 415). Thus, the reverse pawl wheel (412) will restrict the possible positions of the uptake spool (400) to specific 15 degree increments relative to the outer housing when the cover is closed. As described above, the uptake spool (400) is geared to cause a 360 degree rotation of the displacement sensor wheel (430) for a 105 degree rotation of the uptake spool (400), corresponding to a full dose advancement. 105 degree rotation of the uptake spool (400) corresponds to 105/360×24 gear teeth, which is 7 gear teeth. Since a 15 degree rotation of the uptake spool (400) corresponds to $1/7^{th}$ of a full dose advancement, then it also corresponds to $1/7^{th}$ of a complete rotation of the displacement sensor wheel (430) or about 51.4 degrees. Thus, any partial advance and reclosing of the mouthpiece cover can only advance the displacement sensor in increments of about 51.4 degrees.

This can be further explained with reference to FIG. 11 which shows the pin (434) on the displacement sensor (430) in its initial position directly opposed to the Geneva wheel (440). The phantom circles show the 6 other potential resting locations (436a,b,c,d,e,f) for the pin (434) uniformly spaced about the circumference of the displacement sensor (430). The lobes (442) on the Geneva wheel (440) interact (i.e., they movably engage) with the pin (434) on the displacement sensor (430) over a defined range of positions. Over this range of positions the advancing motion of the displacement sensor (430) causes an intermittent or stepwise motion of the Geneva wheel (440) and thus the units wheel (450). This defined range of positions may be referred to as the changeover interval of the Geneva wheel (440). During the changeover interval the displacement sensor is engaged with the Geneva wheel (440) and the units wheel (450) will be in a state of partial advancement (as in FIG. 7c). In a preferred embodiment, the lobes (442) on the Geneva wheel (440) are shaped so that this changeover interval is less than the distance between the resting locations for the pin (434). During assembly of the dose counter, it is ensured that no resting position can occur while the lobes (442) on the Geneva wheel (440) interact with the pin (434) on the displacement sensor (430), e.g., by positioning the pin directly opposed from the Geneva wheel. For example, in the embodiment described above the changeover interval is selected to be less than 51.4 degrees. In practice, this means that whenever the mouthpiece cover is closed, the displacement sensor (430) will not be engaged with the Geneva wheel and thus the units wheel (450) will display a single numeral within the viewing window (320). During normal, complete dose advancement, the pin (434) on the displacement sensor (430) will rest directly opposed from the Geneva wheel. If a patient advances a partial dose, then the pin (434) will come to rest at one of the other potential resting locations (436a,b,c,d,e,f). This enables the dose counter to retain an accurate count of the total number of doses advanced (including any fractional dose), but prevents the units wheel (450) from displaying a partially advanced numeral.

For example, if the pin (434) is initially in the position shown in FIG. 11 and the patient advances $2/7^{th}$ of a dose and recloses the cover, then the pin (434) would come to rest at the position shown in FIG. 11 as 436b. Thus the counter would in essence keep track that $2/7^{th}$ of a dose had been advanced, but the units wheel (450) would not have registered a change in displayed numeral. Should the patient again advance $2/7^{th}$ of a dose and reclose the cover, then the pin (434) would now come to rest at the position shown in FIG. 11 as 436d. The counter would now be keeping track that a total of $4/7^{th}$ of a dose had been advanced, and the units wheel (450) would have advanced (or decremented) by one. Should the patient now advance complete doses for the remainder of the life of the unit, then the pin (434) would continue to come to rest in the position shown in FIG. 11 as 436d and the units wheel (450) would advance (or decrement) a single digit for each complete dose advancement. It should be apparent from the above description that any combination of partial or full dose advancements will be accurately counted and displayed, as the counter will keep track of partial advances and register discrete dose counts on the units wheel.

It should be understood that it is not necessary that 24 ratchet teeth and a 5-lobe Geneva wheel be employed, but that any other suitable combination of fixed ratchet spacings, displacement sensor gearing, and Geneva wheel changeover interval may be selected, as described above, to effect the same result, so long as the distance between potential resting positions of the pin is greater than the changeover interval of the Geneva. That is, so long as the resting positions lie outside the changeover interval of the Geneva.

Thus it should be clear that the general operation of the embodiment shown in FIGS. 5a,b,c to 9a,b,c is as follows. At rest (i.e., in the closed position, i.e., with the mouthpiece cover closed) the elongate carrier has some slack and the displacement sensor is in a nominal starting position that is not engaged with the Geneva wheel. The opening motion of the mouthpiece cover causes the uptake spool and displacement sensor to rotate until the initial slack in the elongate carrier is taken up, at which time the elongate carrier begins to advance. The carrier is advanced at least a length corresponding to a dose of medicament by completely opening the mouthpiece cover which causes further rotation of the uptake spool which, in turn, causes the displacement sensor to make a full revolution during advancement of the full dose. Thus, when the device is fully open, the displacement sensor has rotated forward by an angle greater than a full revolution (i.e., when considering the partial rotation to take up the slack and the full revolution to advance a dose). Closing of the mouthpiece cover causes the displacement sensor to rotate backwards to its initial starting point (i.e., a net rotation of 360 degrees from where it was before the dosing cycle first started) and returns some slack to the (advanced) elongate carrier. Thus the net motion of the displacement sensor is one full revolution which corresponds to a length of elongate carrier advancement equal to at least one dose.

In more general terms, a predetermined length of advancement of the carrier corresponding to a single dose of medicament will cause the displacement sensor to move forward a predetermined amount. Accurate counting and display of numerals is effected by initially moving the displacement sensor forward by an amount greater than the amount corresponding to the length of advancement of the carrier and then subsequently moving the displacement sensor backwards so that the net movement of the displacement sensor during the combined forwards and backwards motion corresponds to the amount of movement that corresponds to the length of advancement of the carrier.

Although described in detail above for a particular embodiment, a number of other variations may also be employed.

Figure 12A:
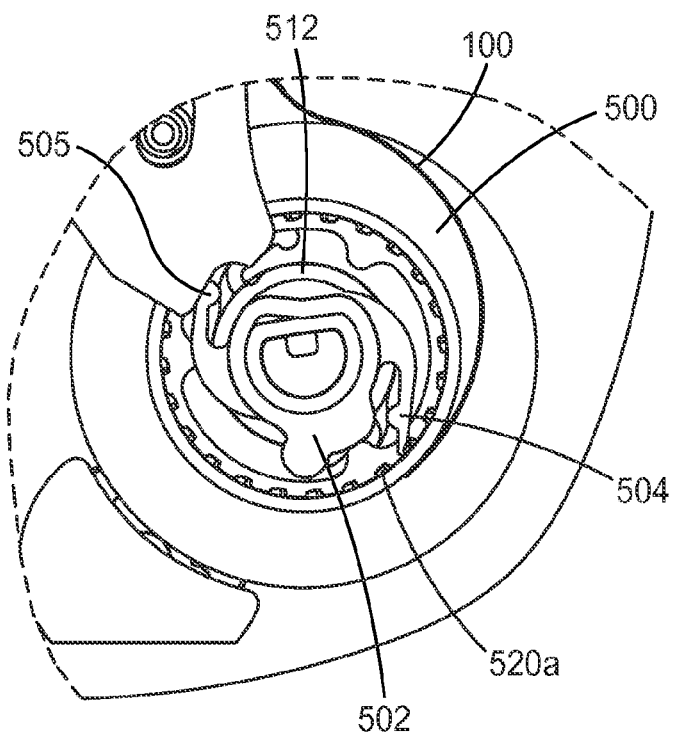
FIG. 12a represents a partial rear view of a detailed portion of a second exemplary device in its closed position.
Figure 12B:
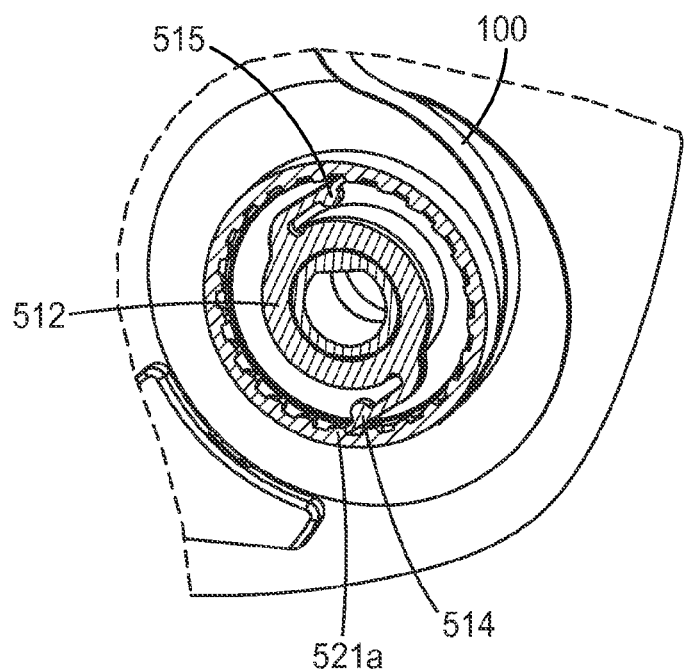
FIG. 12b represents a partial isometric near-to-rear cross sectional view of a detailed portion of the second exemplary device in its closed position.

In another embodiment, shown in FIGS. 12a and 12b, the elongate carrier (100) is shown attached to an uptake spool (500). The uptake spool (500) may be driven forward or advanced (clockwise as shown) by a forward pawl wheel (502) and in particular by two forward pawl wheel arms (504,505) that engage with teeth (one of which is denoted 520a) on the inner hub of the uptake spool (500) that serve as ratchet teeth. The uptake spool (500) may also be engaged by a reverse pawl wheel (512) having two reverse pawl wheel arms (514,515) that may be better seen in the view shown in FIG. 12b. The reverse pawl wheel (512) is fixed in place with respect to the outer housing of the device, in contrast with the embodiment described above wherein the reverse pawl wheel (412) can undergo limited movement with respect to the outer housing. This may be accomplished by a number of means, for example, the reverse pawl wheel (512) may be integrally formed with the outer housing or it may be fixed to an internal carrier component that is in turn fixed to the housing. The general function of the dose counter is as described above with the exception that the reverse pawl wheel (512) does not rotate forward on cover opening and backwards on cover closing. The reverse pawl wheel arms (514,515) still serve to define a fixed position for the uptake spool (500) when the mouthpiece cover is closed, which in turn causes the displacement sensor (not shown) to rest in one of several fixed positions, which prevents the units wheel (450) from displaying a partially advanced numeral.

In another embodiment (not shown), the reverse pawl wheel could be omitted from the previous embodiments, while retaining all of the other components (e.g., Geneva wheel, displacement sensor, etc.). The forward pawl wheel would continue to translate mouthpiece cover rotation into uptake spool rotation during the mouthpiece cover opening. Upon mouthpiece cover closing, the forward pawl wheel arms would slip past the teeth on the uptake spool. A friction brake or other suitable means could be included in the device to prevent backwards rotation of the uptake spool that might otherwise be caused by the friction of the forward pawl wheel arm sliding over the teeth as the mouthpiece cover closed.

This embodiment with a means to prevent backwards rotation would accurately count and display tape advancement.

In another embodiment (not shown), the functions of the Geneva wheel (440) and the units wheel (450) are integrated into a single part. This is accomplished by replacing the gear teeth (452) shown in FIG. 10 on the reverse side of the units wheel (450) with ten Geneva-type lobes. Thus each time the pin (434) on the displacement sensor (430) makes a full revolution it engages a lobe and advances the units wheel (450) one-tenth of a rotation. In essence, the front portion of the integrated part is a units dose display wheel and the back portion is a ten-lobe Geneva wheel.

In another embodiment (not shown), the function of the displacement sensor (430) and the uptake spool are integrated into a single part. For example, the mouthpiece cover rotation angle and the uptake spool size are adjusted, and optionally gears introduced, so that the uptake spool makes a complete rotation for each dose advancement. A pin is placed on the uptake spool to directly engage with the Geneva wheel (440). Other variations would have the uptake spool rotation angle corresponding to a full dose divide equally into 360 degrees, e.g., 180, 120, or 90 degrees of rotation, in which case the uptake spool would have 2, 3, or 4 pins, respectively, so that a pin would advance the Geneva wheel whenever a full dose was advanced.

In another embodiment, the tape could be advanced by the patient twisting a knob, pulling a handle, or pressing a button to advance the tape.

In another embodiment, the pawl arms and the ratchet teeth could be located on the opposite components compared to those that have been described in the embodiments above. That is, the pawl arms may be placed on the inner hub of the uptake spool and point inwards. Corresponding ratchet teeth would then be located on the central hub as part of the cover pivot. In particular, the reverse pawl wheel arms can be integrally formed with the uptake spool and corresponding ratchet teeth could be formed on the outer diameter of the cover pivot.

In one aspect, a predetermined net advancement of the advancement mechanism corresponds to an advancement of the elongate carrier that provides sufficient length to contain a predetermined quantity in the chamber for dispensing. (The predetermined quantity may be a dose, or the dose may comprise a multiple of predetermined quantities if that is what a patient is prescribed to take on each occasion. However, generally the term 'dose' is understood to correspond to a single amount dispensed from a dry powder inhalation device.)

The aforementioned net advancement of the advancement mechanism causes the displacement sensor to move forward a predetermined amount. While the particular gearing may affect the actual distance moved, corresponding movement of these two components enables the displacement sensor to record the net advancement in terms of doses. Accurate counting and display of numerals is effected by initially moving the displacement sensor forward by an amount greater than that corresponding to the predetermined net advancement of the advancement mechanism and then subsequently moving the displacement sensor backwards so that the net movement of the displacement sensor during the combined forwards and backwards motion, which corresponds to the net movement of the advancement mechanism, also corresponds to at least the predetermined quantity of medicament, and the net movement of the advancement mechanism is the same for each such dispensing operation.

When the advancement mechanism is reset, e.g., as a result of closing a mouthpiece cover, the initial part of the resetting causes the displacement sensor to rest in rotationally symmetrical positions relative to the housing (and other parts fixedly engaged with the housing) for every such resetting. Thus, due to these precise positions and the precise gearing between the advancement mechanism and the displacement sensor, the resting location for the displacement sensor is always one of a prescribed number of rotationally symmetrical positions of the displacement sensor.

In dry powder inhalation devices that wind an elongate carrier onto an uptake spool and wherein a dispensing operation comprises turning the spool through a fixed angle, the length wound per dispensing operation may increase as the amount on the uptake spool increases. In certain dry powder inhalation devices of the description, the variation in length wound is kept to a minimum by not allowing the winding diameter to increase much throughout the length of advanced elongate carrier. This is achieved by making the winding diameter at the start large in comparison with the thickness of elongate carrier, and dispenses with the need for a compensation mechanism to equalize the length wound per advancement throughout the length of the elongate carrier. The length wound onto the uptake spool increases from marginally in excess of the predetermined length at the start of the elongate carrier to marginally more in excess at the end of the elongate carrier.

This, along with having a fixed dosing length within the chamber, allows a fixed angle of rotation of the uptake spool (i.e. fixed extent of advancement of the advancement mechanism) to correspond accurately to dispensed doses, and therefore allows the dose counter having movement coordinated therewith to display the number of dispensed doses accurately.

In one embodiment, the description provides a method of dispensing a predetermined quantity of medicament from a dry powder inhalation device. The device comprises a housing defining a chamber, a patient port in communication with said chamber, an elongate carrier carrying medicament, and an advancement mechanism for advancing a length of the elongated carrier into the chamber.

The method comprises moving a length of the elongate carrier forwards into the chamber, the length corresponding to the predetermined quantity of medicament. A length of the elongated carrier is moved forwards with the advancement mechanism, the length corresponding to greater than that needed to provide the predetermined quantity of medicament. Subsequently, the advancement mechanism is moved backwards so that the net length of the elongate carrier moved forwards with the advancement mechanism corresponds to at least the predetermined quantity of medicament and the net movement of the advancement mechanism is the same for each dispensing operation. Medicament is then dispensed from the elongate carrier within the chamber, in such a way that a patient can inhale it through the patient port.

The method may further comprise a method for counting the predetermined quantity of medicament dispensed per dispensing operation. The dry powder inhalation device further comprises a displacement sensor that moves in association with movement of the elongate carrier by the advancement mechanism and a units counter to record a single count for each dispensing operation. The method further comprises converting the net length of the elongate carrier moved by the advancement mechanism, via the displacement sensor, into an advancement of the units counter by one unit.

It is to be understood that where a first component moves in association with a second component, it is meant that any motion of the first is coincident with motion of the second, and that neither can move independently of the other; although the extent of motion may be different e.g., due to gearing.

In another embodiment, the description provides a method of advancing and counting doses in a dry powder inhaler, the dry powder inhaler comprising an elongate carrier carrying medicament, a displacement sensor that moves in association with movement of the elongate carrier by the advancement mechanism, and a units dose counter that moves with movement of the displacement sensor. Advancement of the elongate carrier by a length corresponding to a single dose of medicament will cause the displacement sensor to move forward a predetermined amount. The method comprises the steps of (i) advancing a length of the elongate carrier carrying medicament, wherein the length corresponds to a dose of medicament; (ii) moving the displacement sensor forward with movement of the elongate carrier by the advancement mechanism, wherein the displacement sensor is moved forward by an amount greater than the predetermined amount corresponding to the length of advancement of the elongate carrier; (iii) converting the forward movement of the displacement sensor into advancement of the units dose counter by one unit; and (iv) subsequently moving the displacement sensor backwards so that the net movement of the displacement sensor during the forwards and backwards motion corresponds to the predetermined amount of movement of the advancement mechanism that corresponds to the length of advancement of the carrier.

The invention claimed is:

1. A dry powder inhalation device comprising:
 a housing defining a chamber;
 a patient port in communication with said chamber;
 an elongate carrier carrying medicament;
 an advancement mechanism for advancing a length of the elongate carrier into the chamber;
 a displacement sensor that advances in association with continuous advancement of the elongate carrier; and
 a transfer component that converts the advancement of the displacement sensor into intermittent motion of a units dose display;
 wherein the displacement sensor has a range of movably engaged positions wherein the displacement sensor movably engages the transfer component, and
 the dry powder inhalation device further comprises a discrete alignment mechanism capable of moving the displacement sensor backwards to one of a plurality of spatially defined positions that are not within said range of movably engaged positions.

2. A dry powder inhalation device according to claim 1, further comprising a cover configured to cover the patient port when in a first position, wherein the cover is in mechanical communication with the advancement mechanism such that removing the cover from the patient port advances the advancement mechanism.

3. A dry powder inhalation device according to claim 2 wherein the discrete alignment mechanism comprises a reverse pawl wheel capable of engaging with a post fixed to the device housing.

4. A dry powder inhalation device according to claim 3 wherein the reverse pawl wheel comprises two pawl arms.

5. A dry powder inhalation device according to claim 4 wherein the discrete alignment mechanism comprises a slot in the reverse pawl wheel that is reversibly engageable with a post fixed to the device housing.

6. A dry powder inhalation device according to claim 1 wherein the advancement mechanism comprises a rotatable mouthpiece cover.

7. A dry powder inhalation device according to claim 1 wherein the advancement mechanism comprises an uptake spool.

8. A dry powder inhalation device according to claim 7 wherein the displacement sensor is driven by gears on the uptake spool.

9. A dry powder inhalation device according to claim 1 wherein the displacement sensor comprises a rotatable gear.

10. A dry powder inhalation device according to claim 1 wherein the transfer component comprises a Geneva wheel.

11. A dry powder inhalation device according to claim 10 wherein the Geneva wheel has scallops along its outer edge.

12. A dry powder inhalation device according to claim 1 wherein the units dose display is a geared units dose wheel with numerical indicia on one face of the wheel.

13. A dry powder inhalation device according to claim 12 further comprising a tens dose display comprising a geared tens dose wheel coupled to the units dose wheel and wherein the units dose display and the tens dose display cooperate to indicate a number of doses remaining in the device.

14. A dry powder inhalation device according to claim 13 wherein the tens dose wheel has scallops along its outer edge.

15. A dry powder inhalation device according to claim 1 wherein the elongate carrier is a dimpled tape.

16. A dry powder inhalation device according to claim 1 wherein the displacement sensor moves in association with movement of the elongate carrier.

* * * * *